(12) United States Patent
Fung

(10) Patent No.: US 9,441,962 B2
(45) Date of Patent: Sep. 13, 2016

(54) SHAFT SOUNDING DEVICE FOR MEASURING THICKNESS OF SEDIMENTS AT BASE OF DRILLED SHAFTS

(71) Applicant: Steve Wilhelm Fung, Pikesville, MD (US)

(72) Inventor: Steve Wilhelm Fung, Pikesville, MD (US)

( * ) Notice: Subject to any disclaimer, the term of this patent is extended or adjusted under 35 U.S.C. 154(b) by 99 days.

(21) Appl. No.: 14/594,142

(22) Filed: Jan. 11, 2015

(65) Prior Publication Data

US 2016/0202054 A1    Jul. 14, 2016

Related U.S. Application Data

(60) Provisional application No. 62/047,076, filed on Sep. 8, 2014.

(51) Int. Cl.
G01B 5/18 (2006.01)
G01B 21/08 (2006.01)
G01N 33/24 (2006.01)

(52) U.S. Cl.
CPC ............... *G01B 21/08* (2013.01); *G01N 33/24* (2013.01)

(58) Field of Classification Search
CPC ................................ G01B 21/08; G01N 33/24

USPC ......... 33/1 H, 713, 717, 718, 719, 495, 759, 33/760
See application file for complete search history.

(56) References Cited

U.S. PATENT DOCUMENTS

| | | | | |
|---|---|---|---|---|
| 1,359,763 A | * | 11/1920 | Smith | G01C 13/008 33/720 |
| 2,208,604 A | * | 7/1940 | Scaramucci | E21B 33/16 166/64 |
| 3,786,503 A | * | 1/1974 | Webb | E21F 17/185 200/56 R |
| 3,973,327 A | * | 8/1976 | Cardinale | G01C 15/06 33/1 H |
| 4,712,305 A | * | 12/1987 | Latham | B63B 39/12 33/720 |
| 4,875,295 A | * | 10/1989 | Fleckenstein | G01F 23/0023 33/715 |
| 5,408,893 A | * | 4/1995 | McLeroy | E21B 11/005 175/20 |
| 2011/0278064 A1 | * | 11/2011 | Rasheed | E21B 10/32 175/24 |
| 2012/0152548 A1 | * | 6/2012 | Hinkel | G01N 33/24 166/305.1 |
| 2016/0018307 A1 | * | 1/2016 | Kim | G01N 3/32 73/864.74 |

* cited by examiner

*Primary Examiner* — G. Bradley Bennett

(57) ABSTRACT

A sounding device for measuring the thickness of sediments at the base of dry or wet drilled shaft excavations for the assessment of drilled shaft bottom cleaning operations. The sounding device provides a simple and reliable means to quantitatively evaluate drilled shaft bottom cleanliness.

6 Claims, 2 Drawing Sheets

SHAFT SOUNDING DEVICE FOR MEASURING THICKNESS OF SEDIMENTS AT BASE OF DRILLED SHAFTS

CROSS REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to the assessment of drilled shaft bottom cleaning operations. The invention provides a simple, reliable and quantitative means of measuring the thickness of sediments when accessing drilled shaft base cleanliness.

Drilled shafts are high capacity deep foundation bored piles that are constructed by excavating a hole in the ground and placing fluid concrete within the excavation. Drilled shafts have several advantages over other types of deep foundations, and one of its advantages is the ability to resist high axial loads. The axial load resistance of a drilled shaft is derived for the side resistance of the concreted shafts in the surrounding soils or rock, and from end bearing resistance of the poured concrete on soil or rock. Therefore, the cleanliness of drilled shaft bases is important to achieve the desired end bearing resistance, to limit shaft settlement and to ensure that the poured concrete is not contaminated with sediments.

To achieve the desired end bearing resistance of a drilled shaft, the base of the drilled shaft must be cleaned by personnel lowered into the excavation; by mechanical means such as using a muck-bucket; or by vacuum methods. Drilled shaft base cleanliness criteria are typically specified in construction documents to limit the average thickness of sediments at the excavated shaft base to a maximum of ½ inch to 2 inches. The current state of practice to check the drilled shaft bottom cleanliness is to either: lower personnel to the bottom of the excavation to conduct downhole visual inspection; perform visual inspection using video/camera devices by personnel on the ground surface near the shaft top; or by sounding with a weighted tape lowered by personnel on the ground surface near the shaft top. These methods currently have limitations to the efficiency and effectiveness of assessing shaft bottom cleanliness, such as:

Downhole inspection by personnel lowered to the excavated drilled shaft bottom is typically avoided due to safety concerns and cannot practically be performed in wet drilled shafts.

Visual inspection using video/camera devices is relatively time consuming, uses expensive equipment and requires specialized trained personnel.

Sounding with a weighted tape is quick and easy to perform but determination of sediment thickness is subjective because it's based on a "feel" of how the weight reacts when it strikes the bottom, and is thus subject to interpretation. This can potentially lead to drilled shaft settlement and disputes.

BRIEF SUMMARY OF THE INVENTION

This invention consists of a sounding device and was developed to provide:

A safe, simple, reliable and quantitative method of measuring the thickness of sediments or spoils at the base of a drilled shaft hole.

A more reliable method of assessing drilled shaft bottom cleanliness than sounding with a weighted tape.

A more cost effective method of assessing drilled shaft bottom cleanliness than using visual inspection devices.

The sounding device is designed to measure the thickness of sediments at the bottom of dry and wet drilled shaft excavations. The term sediment used in this specification refers to soil or rock material from the shaft excavation operation that are deposited, disturbed, or accumulated at the base of drilled shafts from the excavation process. The embodiments of the invention are described in the following paragraphs:

An invention for measuring the thickness of sediments at the base of drilled shaft excavations, consisting of: a probe shaft with a probe point at one end and a weighted piston at the other end; a bearing plate and measuring ring centered around the axis of the probe shaft and free to move along the length of the probe shaft; and a measuring tape attachment connected to the weighted piston for lowering and retrieving the invention within the drilled shaft hole. The probe shaft includes a graduated measuring scale.

The embodiments of the invention will improve the state of the current practice. It will measure the sediment thickness at the base of drilled shafts using sounding methods by providing a simple, reliable and quantitative means of measuring the sediment thickness. The invention measures the sediment thickness by using the mass of a weighted piston to push a probe shaft into the sediments, and uses a bearing plate and measuring ring centered around the axis of the probe shaft to measure the distance the probe point penetrates the sediments.

Another embodiment of the invention is to provide a lightweight and portable system for measuring the thickness of the sediment at the base of drilled shafts. The invention is designed to be less than 5 pounds in weight and can be transported, setup, and used by a single operator.

Yet another embodiment of the invention is to provide a reliable system for measuring the thickness of sediments at the base of drilled shafts—where the measurements obtained by the invention are not subject to interpretation and can be duplicated by different operators using the same device.

Other embodiments of the invention also include: the invention is designed to be simple enough to be operated by construction and engineering personnel. It is designed to check shaft bottom cleanliness without the operator entering into the drilled shaft. It is also designed to be more cost effective than visual inspection devices by having a lower cost; less complex to operate, and takes little time to perform the test to determine the sediment thickness at the base of the drilled shafts.

The advantages of the invention include, without limitation: lightweight; low cost; provides quantitative measurements; portable; easy to transport; easy to operate; and measurements can be performed quickly and duplicated.

The invention is not limited by the claims, embodiments and the system descriptions described herein, but is claimed for all embodiments and methods within the scope and spirit of the invention.

BRIEF DESCRIPTION OF THE DRAWINGS

The appended drawings provide an illustration of the invention and provide a clear understanding of its key features as summarized above. It should be noted that the drawings only provide an illustration of the concept of the invention. They should not be considered as the limit of the size, shape or function of the elements used in the invention, as these can be changed based on the type, composition, and thickness of the sediment to be tested. The drawings are not necessarily drawn to scale and are referenced accordingly.

DETAILED DESCRIPTION OF THE INVENTION

Figure 1:
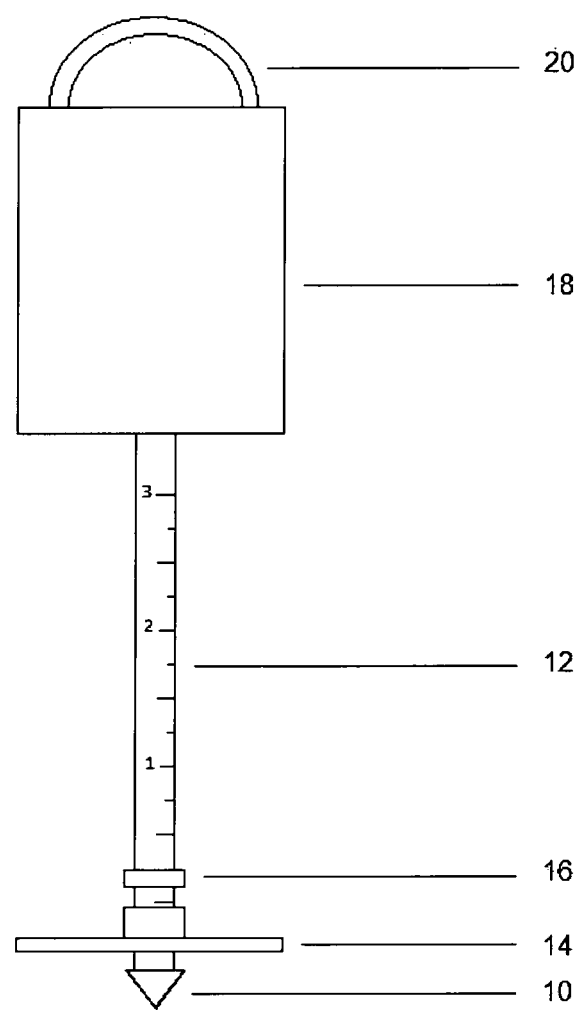
FIG. 1 is an illustration of the invention showing a simplified elevation view.

The invention consists of a sounding device that is designed to measure the thickness of sediments at the base of drilled shaft excavations. The system and features of the sounding device are described in the following paragraphs and the references are on the appended drawings:

FIG. 1 shows the concept of the sounding device. The sounding device includes the following elements:

The probe point 10 is conical (pointed) in shape.

The probe shaft 12 will have a measurement scale annotated on it. The measurement scale will be in either inches or millimeters. The graduated length of the probe shaft 12 will be a minimum of 2 inches. Probe shafts 12 with longer lengths will be used if the thickness of the sediment 22 is expected to exceed 2 inches.

The bearing plate 14 size (diameter) will vary from 1 to 3 inches in diameter and will be mounted on a sleeve to allow free movement along the probe shaft 12 and to prevent tilt of the bearing plate 14. Selection of the bearing plate 14 size will depend on the type of sediment 22 to be tested. Small diameter bearing plate 14 will be used for course sediments 22. Larger diameter bearing plates 14 will be used when fine grained sediments 22 are anticipated.

The measuring ring 16 will be split and fitted close around the probe shaft 12. The measuring ring 16 will be fitted close on the probe shaft 12 so that a force of 0.5 to 1.5 pounds will be required to move it along the probe shaft 12. When measuring ring 16 is pushed up by the bearing plate 14, it will stay in the new position and not move back down by gravity forces after the bearing plate 14 returns to its "zero" position under gravity forces.

The weighted piston 18 will provide the mass necessary to push the probe point 10 through the sediments 22 at the drilled shaft base. The mass of the weighted piston 18 will vary from 2 to 4 pounds.

The measuring tape attachment 20 will allow a measuring tape to be easily attached to the sounding device.

Figure 2:
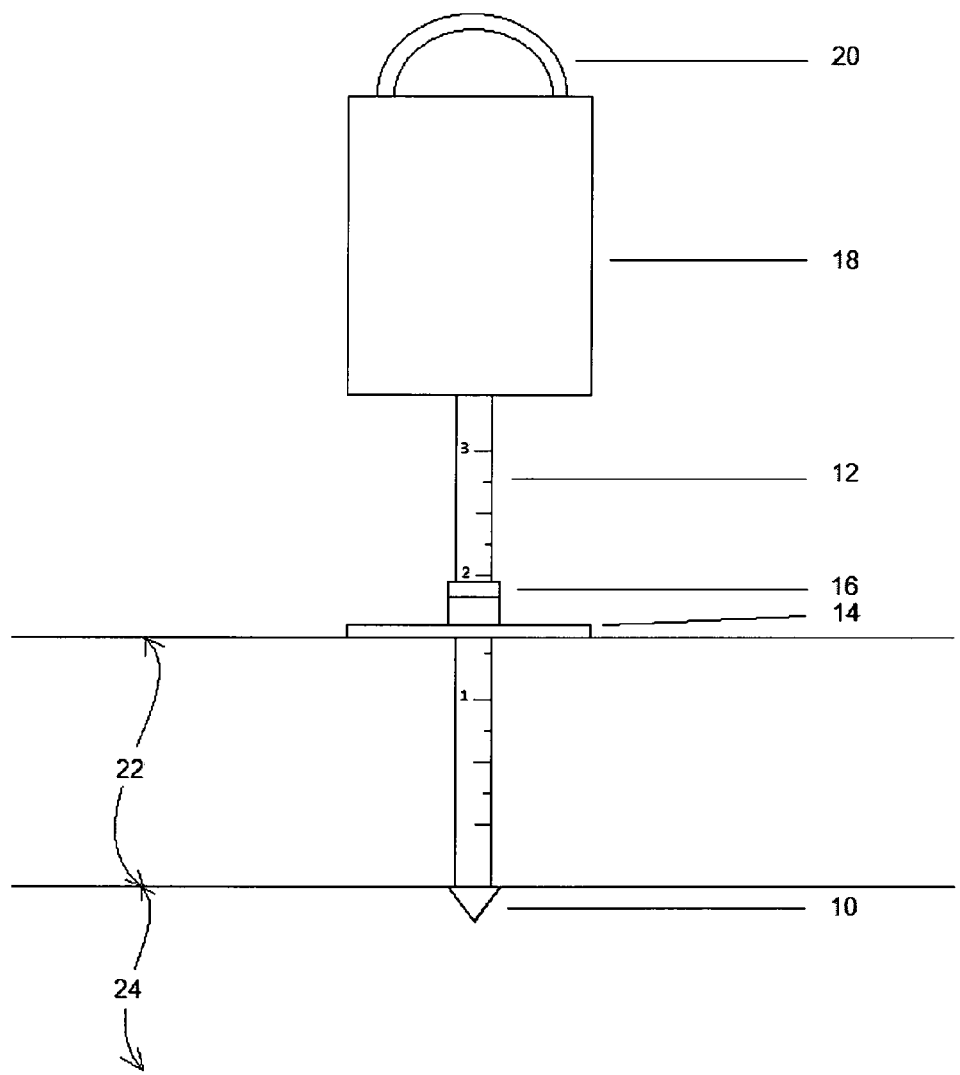
FIG. 2 is an illustration of the invention showing a simplified elevation view of the invention showing the probe point penetrating sediments, the bearing plate on top of the sediments and the measuring ring pushed up by the bearing plate to record the thickness of the sediment.

FIG. 2 shows a simplified elevation view of the sounding device with the probe point 10 penetrating sediments 22, the bearing plate 14 on top of the sediments 22 and the measuring ring 16 pushed up by the bearing plate 14 to record the thickness of the sediment 22. Before lowering the sounding device into the drilled shaft, the measuring ring 16 will first be set to the "zero" location at the top of the bearing plate 14 with the bearing plate 14 at the lowest point on the probe shaft 12. The sounding device will be lowered using a measuring tape to the base of the drilled shaft at a slow rate of descent until it touches the sediments 22 at the bottom of the drilled shaft. After it touches the sediments 22, the sounding device will be raised 2-feet above the sediments 22 and held in place for 5 seconds, or as long as needed, to allow it to stop swinging. The sounding device is then allowed to freefall to penetrate the sediments 22 at the drilled shaft base. When the sounding device strikes the sediment, probe point 10 first, the bearing plate 14 will be suspended on top of the sediments 22 while the probe point 10 will be pushed through the sediments 22 by the weighted piston 18 and will stop on top of the drilled shaft bearing material 24 (firm soil or rock). As the probe point 10 moves down through the sediment 22, the bearing plate 14 will restrain the measuring ring 16 from going down with probe point 10 and probe shaft 12, and will push the measuring ring 16 up along the probe shaft 12—relative to its original location—to a distance equal to the depth of penetration of the probe point 10 through the sediments 22. When the device is raised, the bearing plate 14 will return to its zero position near the probe point 10. However, the measuring ring 16 will remain in place so that when retrieved at the ground surface, the sediment 22 thickness can be determined based on the measuring ring 16 location—distance traveled on probe shaft 12.

The invention claimed is:

1. A sounding device for measuring the thickness of sediments at the base of dry or wet drilled shaft excavation comprising:
   a probe shaft with a graduated measuring scale with a probe point at one end of the probe shaft and a weighted piston at the other end of the probe shaft;
   a bearing plate and a measuring ring centered around the axis of the probe shaft;
   measuring tape attachment on the weighted piston.

2. A sounding device according to claim 1 wherein, the probe shaft comprising a metal rod connected to a weighted piston at one end and a probe point at the other end.

3. The sounding device according to claim 1 wherein, the probe point comprising a conical point, with the base of the cone connected to the probe shaft, having a larger diameter than the probe shaft and tapering to a point.

4. A sounding device according to claim 1 wherein, the weighted piston comprising of 2 to 4 pounds of weight connected to probe shaft at one end and measuring tape attachment at the other end.

5. A sounding device according to claim 1 wherein, the bearing plate comprising a 1" to 3" diameter metal plate connected to a metal tube with an inside diameter larger than the probe shaft; and inside diameter smaller than the base of the probe point and the outside diameter of the measuring ring.

6. A sounding device according to claim 1 wherein, the measuring ring comprising a split ring which, when placed around the probe shaft, requires a force of 0.5 to 1.5 pounds, to move the measuring ring on the probe shaft.

* * * * *